United States Patent
Flego et al.

(10) Patent No.: US 7,341,973 B2
(45) Date of Patent: Mar. 11, 2008

(54) SOLID BASE CATALYST AND USE THEREOF IN BASE CATALYSIS

(75) Inventors: Cristina Flego, Trieste (IT); Mauro Palazzina, Piacenza (IT); Ugo Romano, Vimercate-Milan (IT)

(73) Assignees: Polimeri Europa S.p.A., Brindisi (IT); Enitecnologie S.p.A., San Donato, Milanese-Milan (IT)

( * ) Notice: Subject to any disclaimer, the term of this patent is extended or adjusted under 35 U.S.C. 154(b) by 446 days.

(21) Appl. No.: 10/276,692

(22) PCT Filed: May 15, 2001

(86) PCT No.: PCT/EP01/05579

§ 371 (c)(1),
(2), (4) Date: Nov. 18, 2002

(87) PCT Pub. No.: WO01/87482

PCT Pub. Date: Nov. 22, 2001

(65) Prior Publication Data

US 2003/0171631 A1    Sep. 11, 2003

(30) Foreign Application Priority Data

May 19, 2000    (IT) ............................ MI2000A1112

(51) Int. Cl.
 B01J 21/00    (2006.01)
 B01J 23/40    (2006.01)
(52) U.S. Cl. ..................... 502/233; 502/235; 502/355
(58) Field of Classification Search ............... 502/233, 502/234, 235, 237, 238, 239, 240, 243, 340, 502/341, 344, 349, 355
See application file for complete search history.

(56) References Cited

U.S. PATENT DOCUMENTS

| 5,518,978 A | 5/1996 | Flego et al. |
| 5,602,292 A | 2/1997 | Perego et al. |
| 5,625,115 A | 4/1997 | Flego et al. |
| 5,767,038 A | 6/1998 | Perego et al. |
| 5,908,968 A | 6/1999 | Carati et al. |
| 5,968,344 A | 10/1999 | Perego et al. |
| 5,981,419 A | 11/1999 | Carati et al. |

FOREIGN PATENT DOCUMENTS

| EP | 0 234 498 | 9/1987 |
| EP | 0 492 697 | 7/1992 |
| EP | 0 757 014 | 2/1997 |
| EP | 1 029 582 | 8/2000 |

OTHER PUBLICATIONS

H. Hattori: "Heterogenous basic catalysis" Chemical Reviews, vol. 95, No. 3, pp. 537-558 1995, no month.

T. López, et al., Materials Letters, vol. 38, pp. 283-288, "Acidic-Base Properties of Silica-Magnesia Sol-Gel Mixed Oxides: Use of 2 Butanol as Test Reaction", Feb. 1999.

*Primary Examiner*—J. A. Lorengo
*Assistant Examiner*—Elizabeth Wood
(74) *Attorney, Agent, or Firm*—Oblon, Spivak, McClelland, Maier & Neustadt, P.C.

(57) ABSTRACT

The present invention relates to solid base catalysts consisting of an amorphous material obtained from a silica or alumina gel containing an alkaline, earth-alkaline or transition metal (M), characterized by a molar ratio between metal (M) and Si or Al ranging from 30:1 to 0.0001:1, a surface area ranging from 100 to 600 $m^2/g$, an overall pore volume ranging from 0.1 to 1.1 ml/g, an average channel diameter ranging from 30 to 150 Å and a density of the base sites ranging from 10 to 900 µmol/g. Said catalysts can be conveniently used in base catalysis reactions.

17 Claims, No Drawings

SOLID BASE CATALYST AND USE THEREOF IN BASE CATALYSIS

The present invention relates to solid base catalysts consisting of an amorphous material obtained from a silica or alumina gel containing an alkaline, earth-alkaline or transition metal (M).

The invention also relates to a process for their preparation and their use in base catalysis processes.

Base catalysts have been known in literature for some time, for their applications in numerous reactions of industrial interest as specified by K. Tanabe and W. F. Hölderich in Applied Catalysis vol. 181 (1999), page 399.

Solid base catalysts, on the contrary, are less known due to the fact that they have not been studied to such a wide extent.

Numerous catalytic reactions have been identified in the last few years, in which solid base catalysts have proved to be capable of producing interesting results in terms of performance (activity and selectivity).

In particular, it has been found that solid base catalysts can be used in the fine chemical, pharmaceutical and cosmetic industries as substitutes for homogeneous base catalysts in already consolidated reactions such as isomerizations, additions, alkylations and cyclizations.

Furthermore they can also be used in the petrochemical and refining fields as potential substitutes for acid catalysts in aldol condensation or oligomerization.

Finally, they can be used as alternative reaction catalysts, allowing products of interest to be obtained, starting from different reagents from those of acid-catalyzed reactions such as the production of styrene from toluene, or as catalysts indispensable for some reactions such as the transformation of hetero-rings.

The category of solid base catalysts comprises various groups such as, for example, metal oxides, zeolites, supported alkaline ions, mixed oxides and mineral clays (H. Hattori, Chemical Review, vol. 95 (1995) page 537).

Solid base catalysts are defined as such for their capacity of accepting a proton or donating an electronic doublet.

In mixed oxides, for example, the base origin can be attributed to the presence of ionic pairs with a different coordination number.

The catalytic properties of solid base catalysts are strictly associated with the quantity and strength of the base sites existing on the surface, even though other factors should also be taken into consideration, such as surface area and porosity, as indicated in literature, for example by F. Yagi, H. Tsuij, H. Hattori in Mesoporous Materials, vol. 9 (1997), page 237.

The quantity and strength of the base sites are conveniently determined by the adsorption of a probe molecule such as $CO_2$, on the basis of what is described by H. Hattori in Chemical Review, vol. 95 (1995) page 537.

Catalysts consisting of mixed oxides are generally prepared using various methods such as co-precipitation, co-gelation or blending, as specified by H. Hattori in Chemical Review, vol. 95 (1995) page 537.

It is known, however, that the above preparation methods, in the case of mixed oxides with a binary composition and containing Si or Al, only allow catalysts with base characteristics to be obtained in certain cases, thus limiting the availability of potentially interesting compositions for base catalysis.

For example, mixed oxides based on Si/Al, Mo/Si, Fe/Si, Zr/Si, have acid characteristics, those based on Zn/Si and Mg/Si, have acid-base characteristics, those based on Mg/Al and Zn/Al have acid-base characteristics, whereas Ti/Al and Mo/Al are acid, as specified by K. Tanabe, M. Misono, Y. Ono, H. Hattori in Studies Surface Science and Catalysis, vol. 51 (1989) chap. 1 and 3.

New base catalysts have now been found, consisting of mixed oxides and containing Si or Al, which, although having a composition similar to that of the catalysts described in the known art, have structural characteristics and a base distribution which are such as to enable them to be conveniently used in base catalysis reactions.

An object of the present invention therefore relates to solid base catalysts consisting of an amorphous material obtained from a silica or alumina gel containing an alkaline, earth-alkaline or transition metal (M), characterized by a molar ratio between metal (M) and Si or Al ranging from 30:1 to 0.0001:1, a surface area ranging from 100 to 600 $m^2/g$, an overall pore volume ranging from 0.1 to 1.1 ml/g, an average channel diameter ranging from 30 to 150 Å and a density of the base sites ranging from 10 to 900 µmol/g.

A further object of the present invention relates to the process for the preparation of the above catalysts which comprises the dissolution and mixing at a temperature ranging from 21 to 80° C. of a precursor of an alkaline, earth-alkaline or transition metal (M), of a precursor of Si or Al in the form of an inorganic salt or alkoxy-derivative and a templating agent, until a gel is formed, which is subsequently aged, dried and then calcined in air.

When a precursor of Si is used, the dissolution and mixing are carried out as follows:

a) dissolution of the alkaline, earth-alkaline or transition metal in alcohol;
b) addition of the Si precursor in the form of an inorganic salt or alkoxy derivative;
c) addition of the aqueous solution containing the templating agent.

When, on the other hand, a precursor of Al is used, the following procedure is adopted:

a) dissolution of the precursor of Al in the form of an inorganic salt or alkoxy derivative in alcohol;
b) addition of an aqueous solution, in which the precursor of the alkaline, earth-alkaline or transition metal and the templating agent are present.

The various components are present in the mixture in the following molar ratios:

| | |
|---|---|
| M/Si or Al | from 30/1 to 0.0001/1 |
| Templating agent/$SiO_2$ or $Al_2O_3$ | from 3.5/1 to 0.05/1 |
| $H_2O$/$SiO_2$ or $Al_2O_3$ | from 1500/1 to 0.05/1 |
| and preferably: | |
| M/Si or Al | from 20/1 to 0.001/1 |
| Templating agent/$SiO_2$ or $Al_2O_3$ | from 1/1 to 0.1/1 |
| $H_2O$/$SiO_2$ or $Al_2O_3$ | from 30/1 to 1/1 |

The time for complete gelation varies in relation to the temperature and concentration of the reagents; the gelation generally takes place within a time range of 15 minutes to 16 hours and typically within a range of 20-120 minutes.

The gel obtained according to the process of the invention is collected with a pallet and left under stirring at a temperature varying from 21 to 80° C.

It is then subjected to an aging phase at room temperature for 16-20 h.

It is subsequently dried in an oven at temperatures varying from 100 to 150° C. and preferably within the range of 100-120° C., for a time sufficient to eliminate the water.

Finally, it is calcined operating in an oxidizing atmosphere, for example in air.

The calcination temperatures vary within a range of 500 to 700° C. and are preferably in the order of 550-600° C. The calcination times can vary from 4 to 20 hours and are typically in the order of 4-8 hours.

Tetra-ethyl, n-propyl or n-butyl ammonium hydroxide are preferably used as templating agent.

Silicon precursors which can be used are preferably tetra-alkyl silicates such as tetra-ethyl silicate, for example.

Aluminum compounds which can be used are preferably aluminum trialkoxides, such as aluminum tri sec-butoxide and aluminum tri iso-propoxide.

The metal is an alkaline (IA), earth-alkaline (IIA) or transition (IVB) metal and preferably consists of potassium, magnesium, calcium, barium, cesium, zirconium, whereas the precursors are compounds of the metal, preferably acetates, ethoxides, propoxides, nitrates, carbonates, hydroxides, depending on the specific solubilities.

A silica (or alumina) gel is thus obtained, containing an alkaline, earth-alkaline or transition metal, according to the present invention, which has an amorphous structure and a ratio between the first element (selected from one of the alkaline, earth-alkaline or transition metals) and silicon or aluminum equal to that deriving from the compounds of one of the alkaline, earth-alkaline or transition metals and silicon or aluminum initially charged and within the range of 30/1 to 0.0001/1 and preferably from 20/1 to 0.001/1.

Said silica (or alumina) gel comprising one of the alkaline, earth-alkaline or transition metals has a surface area (determined with the BET method) which varies from 100 to 600 m$^2$/g. The overall pore volume is within the range of 0.1-1.1 ml/g.

The pores are within the mesopore range, with an average diameter varying from 30 to 150 Å. The density of the base sites (determined by $CO_2$ adsorption) varies from 10 to 900 μmol/g.

The gel of the present invention is catalytically active in reactions catalyzed by bases, such as those used for the conversion of hydrocarbons, according to what is known and described for example by H. Hattori, Chem. Rev. 95 (1995) 537.

Examples of these reactions are: oligomerization of olefins, dehydrogenation of cumene to alpha-methylstyrene, selective hydrogenation of conjugated dienes, isomerization of alkenes, dimerization of olefins, double bond migration, dehydrations and dehydrogenations, cyclizations, aldol condensation, dehydrocyclodimerization of conjugated dienes, alkylation of aromatics on the side-chain, amination, Meerwein-Ponndorf-Verley reduction, Tishchenko reaction, Michael addition, Witteg-Horner reaction, Knoevenagel condensation, synthesis of α,β-unsaturated compounds, NO reduction and oxidative coupling of methane.

The catalysts according to the invention can be used as such or in a combination with suitable metal oxides which act as ligands.

Oxides suitable for the purpose can be silicas, aluminas, titanium, magnesium and zirconium oxides.

The gels of one of the alkaline, earth-alkaline or transition metals and silicon (or aluminum) can be mixed in weight ratios ranging from about 30:70 to 95:5 and preferably from 50:50 to 70:30.

The two components can be mixed with the conventional techniques and the mixture can be consolidated into the desired end-form, for example in the form of extruded or granulated products.

Operating in this way, it is possible to give the catalysts better mechanical characteristics.

The catalysts according to the present invention can be used with good results in double bond migration reactions.

For example, cis-2-butene can be obtained, starting from 1-butene in predominant quantities with respect to trans-2-butene.

According to what is specified by H. Hattori in Chemical Review, vol. 95 (1995) page 537, a high cis/trans ratio is observed in isomerization reactions catalyzed by bases, whereas the ratio is close to 1 in reactions catalyzed by acids.

According to what is indicated by H. Pines and W. M. Stalick in "Base-catalyzed reactions of hydrocarbons and related compounds" chap. 2 (Academic Press, New York, 1977), the double bond isomerization reactions can be carried out within a temperature range of −30° C. to 260° C. depending on the reagent used.

In the case of 1-butene, the temperature preferably ranges from −30 to 200° C.

The reaction can be carried out in an autoclave, where the solid catalyst in powder form is introduced in quantities varying from 0.5 to 2 g, after being activated in a stream of inert gas (for example, helium) at a temperature ranging from 500 to 600° C. for a time varying from 1 to 3 h.

1-butene is then fed and the system is brought to a pressure of 2-10 Bars and a temperature of 20-200° C., preferably from 50 to 100° C.

After a period of time ranging from 1 to 24 hours, preferably from 2 to 5 hours, 2-butenes are obtained in which the ratio between the cis/trans forms is always higher than 1.1.

The catalyst of the present invention can also be conveniently used in the re-arrangement reaction of cyclo-alkanes to give alpha-olefins.

It is possible to obtain, for example, 1-octene by means of a base-catalyzed re-arrangement reaction of cyclo-octane.

This reaction involves the opening of the ring and the formation of a linear product with a double bond in alpha position.

Secondary reactions can also take place, such as: (i) the formation of branched products, (ii) cracking, (iii) shifting of the double bond to an internal position.

The transformation of cyclo-octane to 1-octene is limited by thermodynamic equilibria.

In fact, the quantity of 1-octene increases with an increase in the temperature and varies from 3 to 5% within the range of 350-550° C., with a ratio between the cis and trans-2-octene and 1-octene isomers ranging from 13.4 to 7.7.

Some illustrative but non-limiting examples are provided for a better understanding of the present invention and for its embodiment.

EXAMPLE 1

39.9 g of aluminum tri sec-butoxide (Al(OC$_4$H$_9$)$_3$) are dissolved in 50 ml of isopropanol at room temperature. 3.4 g of Mg acetate are slowly added to an aqueous solution of 15.3 g of tetrapropylammonium hydroxide (TPAOH) at 30% by weight, again at room temperature. As soon as the aqueous solution is added to the alcoholic solution at room temperature, a gel is immediately formed, which is collected with a pallet and left under stirring at about 60° C. The composition of the mixture thus obtained is the following:

| | |
|---|---|
| Mg/Al = | 0.15 |
| TPAOH/Al$_2$O$_3$ = | 0.28 |
| H$_2$O/Al$_2$O$_3$ = | 15.4 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the magnesium and aluminum initially charged.

The Infra-red (IR) spectrum of the material, registered with a Perkin Elmer spectrometer mod. 2000, confirms the completely amorphous nature of the gel. XRD analysis of the material also shows the absence of signals which can be attributed to an orderly crystalline structure.

The surface area of the material, measured by means of N$_2$ physical-absorption at −196° C. with a Fisons Carlo Erba Sorptomatic 1990 instrument and calculated with the BET method, proved to be 390 m$^2$/g with an overall pore volume of 1.08 ml/g and average pore diameter of 76 Å, calculated with the Dollymore-Heal model.

The density of the base sites is determined by means of CO$_2$ absorption with the pulse dynamic method, effected with a Micromeritics PulseChemisorb 2705 instrument. The density of the base sites of the material based on magnesium and aluminum is 160 µmol/g.

EXAMPLE 2

40.5 g of aluminum tri sec-butoxide (Al(OC$_4$H$_9$)$_3$) are dissolved in 50 ml of isopropanol at room temperature. 0.24 g of Mg acetate are slowly added to an aqueous solution of 15.6 g of tetrapropylammonium hydroxide (TPAOH) at 19.2% by weight, again at room temperature. As soon as the aqueous solution is added to the alcoholic solution at room temperature, a gel is immediately formed, which is collected with a pallet and left under stirring at about 60° C. The composition of the mixture thus obtained is the following:

| | |
|---|---|
| Mg/Al = | 0.001 |
| TPAOH/Al$_2$O$_3$ = | 0.18 |
| H$_2$O/Al$_2$O$_3$ = | 8.5 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the magnesium and aluminum initially charged. The material is confirmed to be completely amorphous. The surface area is 410 m$^2$/g, the overall pore volume 0.66 ml/g and the average pore diameter 50 Å.

The density of the base sites is 176 µmol/g.

EXAMPLE 3

39.4 g of aluminum tri sec-butoxide (Al(OC$_4$H$_9$)$_3$) are dissolved in 50 ml of isopropanol at room temperature. A solution of 20.63 g of tetrapropylammonium hydroxide (TPAOH) at 30% by weight is added to 6.7 g of water, and 45.7 g of Mg acetate are then slowly dissolved, again at room temperature. As soon as the aqueous solution is added to the alcoholic solution at room temperature, a gel is immediately formed, which is collected with a pallet and left under stirring at about 60° C. The composition of the mixture thus obtained is the following:

| | |
|---|---|
| Mg/Al = | 2.0 |
| TPAOH/Al$_2$O$_3$ = | 0.38 |
| H$_2$O/Al$_2$O$_3$ = | 27.8 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the magnesium and aluminum initially charged. The material is confirmed to be completely amorphous. The surface area is 280 m$^2$/g, the overall pore volume 0.25 ml/g and the average pore diameter 30 Å.

The density of the base sites is 249 µmol/g.

EXAMPLE 4

39.4 g of aluminum tri sec-butoxide (Al(OC$_4$H$_9$)$_3$) are dissolved in 50 ml of isopropanol at room temperature. The solution is subsequently heated to 60° C. and 11.2 g of zirconium tetra isopropoxide (Zr(OC$_3$H)$_{-4}$) are dissolved. An aqueous solution of 23.1 g of tetrapropylammonium hydroxide (TPAOH) at 19.2% by weight is added. As soon as the aqueous solution is added to the alcoholic solution at room temperature, a gel is immediately formed, which is collected with a pallet and left under stirring at 60° C.

The composition of the mixture thus obtained is the following:

| | |
|---|---|
| Zr/Al = | 0.15 |
| TPAOH/Al$_2$O$_3$ = | 0.27 |
| H$_2$O/Al$_2$O$_3$ = | 13.0 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the zirconium and aluminum initially charged. The material is confirmed to be completely amorphous. The surface area is 350 m$^2$/g, the overall pore volume 0.47 ml/g and the average pore diameter 44 Å. The density of the base sites is 176 µmol/g.

EXAMPLE 5

39.4 g of aluminum tri sec-butoxide (Al(OC$_4$H$_9$)$_3$) are dissolved in 50 ml of isopropanol at room temperature. A solution of 14.9 g of tetrapropylammonium hydroxide (TPAOH) at 30% by weight is added to 11.4 g of water, and 5.9 g of Ca nitrate are slowly dissolved, again at room temperature. As soon as the aqueous solution is added to the alcoholic solution at room temperature, a gel is immediately formed, which is collected with a pallet and left under stirring at about 60° C. The composition of the mixture thus obtained is the following:

| | |
|---|---|
| Ca/Al = | 0.15 |
| TPAOH/Al$_2$O$_3$ = | 0.27 |
| H$_2$O/Al$_2$O$_3$ = | 8.3 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the calcium and aluminum initially charged. The material is confirmed to be completely amorphous. The surface area is 240 m$^2$/g, the overall pore volume 0.54 ml/g and the average pore diameter 70 Å. The density of the base sites is 286 µmol/g.

EXAMPLE 6

39.4 g of aluminum tri sec-butoxide (Al(OC$_4$H$_9$)$_3$) are dissolved in 50 ml of isopropanol at room temperature. The solution is subsequently heated to 60° C. and 6.4 g of Ba acetate are dissolved. An aqueous solution of 5.6 g of water and 23.1 g of tetrapropylammonium hydroxide (TPAOH) at 19.2% by weight is added. As soon as the aqueous solution is added to the alcoholic solution at room temperature, a gel is immediately formed, which is collected with a pallet and left under stirring at 60° C. The composition of the mixture thus obtained is the following:

| | |
|---|---|
| Ba/Al = | 0.15 |
| TPAOH/Al$_2$O$_3$ = | 0.27 |
| H$_2$O/Al$_2$O$_3$ = | 15.0 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the barium and aluminum initially charged. The material is confirmed to be completely amorphous. The surface area is 240 m$^2$/g, the overall pore volume 0.57 ml/g and the average pore diameter 75 Å. The density of the base sites is 112 µmol/g.

EXAMPLE 7

40.5 g of aluminum tri sec-butoxide (Al(OC$_4$H$_9$)$_3$) are dissolved in 50 ml of isopropanol at room temperature. 2.4 g of K acetate are slowly added to an aqueous solution of 28.3 g of tetrapropylammonium hydroxide (TPAOH) at 19.2% by weight, again at room temperature. As soon as the aqueous solution is added to the alcoholic solution at room temperature, a gel is immediately formed, which is collected with a pallet and left under stirring at about 60° C. The composition of the mixture thus obtained is the following:

| | |
|---|---|
| K/Al = | 0.15 |
| TPAOH/Al$_2$O$_3$ = | 0.33 |
| H$_2$O/Al$_2$O$_3$ = | 15.9 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the potassium and aluminum initially charged. The material is confirmed to be completely amorphous. The surface area is 250 m$^2$/g, the overall pore volume 0.40 ml/g and the average pore diameter 66 Å. The density of the base sites is 653 µmol/g.

EXAMPLE 8

33.5 g of tetra-ethyl-silicate (Si(OC$_2$H$_5$)$_4$) are dissolved in 210 ml of ethanol at room temperature. A solution of 15.4 g of tetrapropylammonium hydroxide (TPAOH) at 30% by weight is added to 11.4 g of water, and 11.4 g of magnesium acetate are slowly dissolved, again at room temperature. As soon as the aqueous solution is added to the alcoholic solution at room temperature, a gel is immediately formed, which is collected with a pallet and left under stirring at about 60° C. The composition of the mixture thus obtained is the following:

| | |
|---|---|
| Mg/Si = | 0.5 |
| TPAOH/SiO$_2$ = | 0.28 |
| H$_2$O/SiO$_2$ = | 14.2 |

After about 1 hour under stirring, the homogeneous gel produced is left to age at room temperature for a night (about 16 hours). It is subsequently dried in an oven at 120° C. for 2 hours and calcined at 550° C. for 4 hours in air.

A product is obtained with a quantitative yield with respect to the magnesium and silicon initially charged. The material is confirmed to be completely amorphous. The surface area is 520 m$^2$/g, the overall pore volume 0.55 ml/g and the average pore diameter 135 Å. The density of the base sites is 42 µmol/g.

EXAMPLE 9 (Comparative Example)

A material is prepared starting from commercial γ alumina (Akzo, Al$_2$O$_3$ 000 –1.5 E, surface area of 374 m$^2$/g) as carrier and using the conventional aqueous impregnation procedure, for effecting a comparison with the material of Example 7.

10.5 g of carrier are put in contact using the wetness imbibition method with a 5.5 M aqueous solution of KOH for 16 h at room temperature. This is followed by drying and calcination as in Example 7. The material obtained has a nominal content of 2.6 mmol/g of K.

The density of the base sites is 69 µmol/g and is compared with the catalyst of Example 7 having an analogous composition.

EXAMPLE 10

The catalyst of Example 4 was tested in the double bond migration reaction of 1-butene in a test carried out in an autoclave.

1 g of solid catalyst in powder form is activated in a stream of helium at 500° C. for 2 h. At the end of the pre-treatment, the catalyst is cooled and transferred to the autoclave having a volume of 100 ml, in dry box. 1-butene is fed and the system is brought to a pressure of 2 Bars and a temperature of 100° C. After 3 hours, the ratio between the 2-butenes produced is cis/trans=2.37, upon chromatographic analysis.

EXAMPLE 11

The catalyst of Example 8 was tested in the double bond migration reaction of 1-butene in a test carried out in an autoclave.

1 g of solid catalyst in powder form is activated in a stream of helium at 500° C. for 2 h. At the end of the pre-treatment, the catalyst is cooled and transferred to the autoclave having a volume of 100 ml, in dry box. 1-butene is fed and the system is brought to a pressure of 2 Bars and a temperature of 100° C. After 3 hours, the ratio between the 2-butenes produced is cis/trans=1.54, upon chromatographic analysis.

EXAMPLE 12

The catalyst of Example 1 was tested in the double bond migration reaction of 1-butene in a test carried out in an autoclave.

1 g of solid catalyst in powder form is activated in a stream of helium at 500° C. for 2 h. At the end of the pre-treatment, the catalyst is cooled and transferred to the autoclave having a volume of 100 ml, in dry box. 1-butene is fed and the system is brought to a pressure of 2 Bars and a temperature of 100° C. After 3 hours, the ratio between the 2-butenes produced is cis/trans=3.62, upon chromatographic analysis.

EXAMPLE 13

The catalyst of Example 7 was tested in the re-arrangement reaction of cyclo-octane in a fixed bed reactor under the conditions described below.

2.5 g of solid catalyst, ground to 20-40 mesh, is charged into the reactor in the center of the isotherm zone of the oven using an appropriate porous septum. The catalytic test is preceded by an activation treatment at a temperature of 500° C. in a stream of nitrogen for 4 hours.

At the end of the pre-treatment, the reactor is cooled to room temperature, cyclo-octane is fed at 0.37 ml/min and the system is brought to a pressure of 40 Bars and a temperature of 470° C.

The products obtained in the re-arrangement reaction of cyclo-octane were analyzed by means of gaschromatography. The conversion is equal to 16.6%, the selectivity to 1-octene is 15%, with a ratio between the 2-octene and 1-octene cis and trans isomers of 1.2.

The invention claimed is:

1. Solid base catalysts consisting of an amorphous material obtained from a silica gel comprising an alkaline or earth-alkaline metal (M), or alumina gel comprising an alkaline, earth-alkaline or transition metal (M), wherein a molar ratio between metal (M) and Si or Al ranging from 30:1 to 0.0001:1, and wherein said amorphous material has a surface area ranging from 100 to 600 m²/g, an overall pore volume ranging from 0.1 to 1.1 ml/g, an average channel diameter ranging from 30 to 150 Å, and a density of the base sites ranging from 10 to 900 μmol/g.

2. A process for the preparation of the catalysts according to claim 1, which comprises the dissolution and mixing at a temperature ranging from 21 to 80° C. of a precursor of an alkaline, earth-alkaline or transition metal (M), of a precursor of Si or Al in the form of an inorganic salt or alkoxy-derivative and a templating agent, until a gel is formed, which is subsequently aged, dried and then calcined in air.

3. The process according to claim 2, wherein, when operating in the presence of a precursor of Si, the dissolution and mixing are carried out as follows:

a) dissolution of the alkaline, earth-alkaline or transition metal in alcohol;
   b) addition of the Si precursor in the form of an inorganic salt or alkoxy derivative; and
   c) addition of the aqueous solution containing the templating agent.

4. The process according to claim 2, wherein, when operating in the presence of a precursor of Al, the dissolution and mixing are carried out as follows:

a) dissolution of the precursor of Al in the form of an inorganic salt or alkoxy derivative in alcohol; and
   b) addition of an aqueous solution, in which the precursor of the alkaline, earth-alkaline or transition metal and the templating agent are present.

5. The process according to claim 2, wherein the components of the mixture are present in the following molar ratios:

M/Si or Al from 30/1 to 0.0001/1;
   Templ. agent/$SiO_2$ or $Al_2O_3$ from 3.5/1 to 0.05/1; and
   $H_2O$/$SiO_2$ or $Al_2O_3$ from 1500/1 to 0.05/1.

6. The process according to claim 5, wherein the components of the mixture are present in the following molar ratios:

M/Si or Al from 20/1 to 0.001/1;
   Templ. agent/$SiO_2$ or $Al_2O_3$ from 3/1 to 0.1/1; and
   $H_2O$/$SiO_2$ or $Al_2O_3$ from 30/1 to 1/1.

7. The process according to claim 2, wherein the metal is selected from the group consisting of potassium, magnesium, calcium, barium, cesium, zirconium, and the precursors of the metal (M) are compounds selected from the group consisting of acetates, ethoxides, propoxides, nitrates, carbonates, hydroxides.

8. The process according to claim 2, wherein the silicon precursor is tetra-ethylsilicate and the aluminum precursor is aluminum tri sec-butoxide or aluminum tri iso-propoxide.

9. The process according to claim 2, wherein the templating agent is selected from tetra-ethyl, n-propyl or n-butyl ammonium hydroxide.

10. The process according to claim 2, wherein the gel is aged at room temperature for 16-20 h, dried at temperatures varying from 100 to 150° C. for a time sufficient to eliminate the water and calcined at temperatures within the range of 500 to 700° C. for times varying from 4 to 20 hours.

11. The process according to claim 10, wherein the gel is dried at temperatures ranging from 100-120° C. and calcined at temperatures varying from 550 to 600° C. for a time ranging from 4-8 hours.

12. A process for the preparation of 2-butenes with cis/trans ratio higher than 1:1 comprising carrying out a double bond migration reaction of 1-butene in the presence of the catalysts according to claim 1.

13. A process for the preparation of 1-octene with a ratio between 2-octene and 1-octene cis and trans isomers close to or lower than 2, comprising carrying out a rearrangement reaction of cyclo-octane in the presence of the catalysts according to claim 1.

14. A process for the preparation of 1-hexane comprising carrying out a reaction of cyclo-hexane in the presence of the catalysts according to claim 1.

15. A process for the catalysis of a reaction with a base, comprising adding the solid base catalysts according to claim 1 to reactions catalyzed by bases.

16. The process according to claim 15, wherein the process comprises double bond migration in alpha olefins.

17. The process according to claim 16, wherein the process comprises the preparation of alpha olefins starting from cyclo-alkanes.

* * * * *